(12) United States Patent
Boone et al.

(10) Patent No.: US 11,571,176 B2
(45) Date of Patent: Feb. 7, 2023

(54) MULTIMODAL SYSTEM FOR BREAST IMAGING

(71) Applicant: The Regents of the University of California, Oakland, CA (US)

(72) Inventors: John M. Boone, Sacramento, CA (US); George W. Burkett, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 118 days.

(21) Appl. No.: 17/152,188

(22) Filed: Jan. 19, 2021

(65) Prior Publication Data

US 2021/0219933 A1    Jul. 22, 2021

Related U.S. Application Data

(60) Provisional application No. 62/961,886, filed on Jan. 16, 2020.

(51) Int. Cl.
*A61B 6/00* (2006.01)
*A61B 6/03* (2006.01)
(Continued)

(52) U.S. Cl.
CPC .............. *A61B 6/502* (2013.01); *A61B 6/032* (2013.01); *A61B 6/0414* (2013.01);
(Continued)

(58) Field of Classification Search
CPC ....... A61B 6/502; A61B 6/032; A61B 6/0414; A61B 6/0421; A61B 6/4085;
(Continued)

(56) References Cited

U.S. PATENT DOCUMENTS 7,236,563 B2   6/2007   Sa et al.
8,139,712 B2 * 3/2012   Kojima ................ A61B 6/0414
                                                       378/116
(Continued)

OTHER PUBLICATIONS

Boone et al., "Dedicated breast CT: radiation dose and image quality evaluation", Radiology (2001) 221:657?77.
Chen et al., "Cone-beam volume CT breast imaging: feasibility study", Med. Phys. (2002) 29:755?70.
Reese et al., "Computerized reconstructive tomography applied to breast pathology", Am. J. Roentegnol. (1976) 126:406712.
(Continued)

*Primary Examiner* — Courtney D Thomas
(74) *Attorney, Agent, or Firm* — Venable LLP; Henry J. Daley; Aziz H. Poonawalla

(57) ABSTRACT

A multimodal system for breast imaging includes an x-ray source, and an x-ray detector configured to detect x-rays from the x-ray source after passing through a breast. The system includes an x-ray detector translation system operatively connected to the x-ray detector so as to be able to translate the x-ray detector from a first displacement from the breast to a second displacement at least one of immediately adjacent to or in contact with the breast. The system includes an x-ray image processor configured to: receive a CT data set from the x-ray detector, the CT data set being detected by the x-ray detector at the first displacement; compute a CT image of the breast; receive a mammography data set from the x-ray detector, the mammography data set being detected by the x-ray detector at the second displacement; and compute a mammography image of the breast.

21 Claims, 11 Drawing Sheets

(51) Int. Cl.
    *A61B 6/04*          (2006.01)
    *A61B 34/30*       (2016.01)
    *A61B 10/00*       (2006.01)

(52) U.S. Cl.
    CPC .......... *A61B 6/0421* (2013.01); *A61B 6/4085* (2013.01); *A61B 6/4447* (2013.01); *A61B 6/4452* (2013.01); *A61B 6/461* (2013.01); *A61B 6/467* (2013.01); *A61B 6/54* (2013.01); *A61B 10/0041* (2013.01); *A61B 34/30* (2016.02); *A61B 6/4291* (2013.01); *A61B 6/487* (2013.01)

(58) Field of Classification Search
    CPC ..... A61B 6/4447; A61B 6/4452; A61B 6/461; A61B 6/467; A61B 6/54; A61B 10/0041; A61B 34/30; A61B 6/4291; A61B 6/487; A61B 6/0435; A61B 6/4007; A61B 6/4035; A61B 10/0233
    See application file for complete search history.

(56) References Cited

U.S. PATENT DOCUMENTS

| | | |
|---|---|---|
| 8,792,965 B2 | 7/2014 | Ning et al. |
| 2008/0004526 A1* | 1/2008 | Gross .................. A61B 8/0825 600/437 |
| 2008/0292046 A1 | 11/2008 | Camus et al. |
| 2012/0039436 A1 | 2/2012 | Bothorel et al. |
| 2016/0249872 A1 | 9/2016 | Grass et al. |
| 2018/0008220 A1 | 1/2018 | Boone et al. |

OTHER PUBLICATIONS

Becker et al., "A Prototype Multi-X-ray Source Array (MXA) for digital breast tomosynthesis", Phys. Med. Biol., (2020), vol. 65, 235033. (Published Nov. 27, 2020).

Becker et al., "Cone Beam CT Multisource Configurations: Evaluating Image Quality, Scatter, and Dose Using Phantom Imaging and Monte Carlo Simulations", Phys. Med. Biol., (2020), vol. 65, 235032 (Published Nov. 27, 2020).

\* cited by examiner

MULTIMODAL SYSTEM FOR BREAST IMAGING

CROSS-REFERENCE OF RELATED APPLICATION

This application claims priority to U.S. Provisional Application No. 62/961,886, filed Jan. 16, 2020, the entire contents of which are hereby incorporated by reference.

This invention was made with government support under grant numbers R01CA181081 and R01CA214515 awarded by the National Institute of Health (NIH). The government has certain rights in the invention.

BACKGROUND

1. Technical Field

The currently claimed embodiments of the present invention are directed to medical imaging and guidance systems, and more specifically to breast x-ray imaging and biopsy guidance systems.

2. Discussion of Related Art

While the current state-of-the-art for breast imaging is typically digital mammography, sometimes coupled with limited angle tomography which is often called breast tomosynthesis, it is recognized by the breast imaging community that these two-dimensional or pseudo-three-dimensional imaging modalities do not fully address the needs of breast cancer detection, diagnosis, and evaluation.

Several researchers and corporations have studied the use of computed tomography principles for breast imaging, including early efforts by General Electric (1) and more recent studies by UC Davis (2), Koning Corporation (3), and others. The systems described by these research studies and patents in general describe imaging a single breast at a time with the patient laying prone on the table, with the breast hanging through a hole in that table in so-called pendant position.

None of these breast computed tomography (CT) based systems, however, include the ability of the imaging system to produce mammograms in addition to fully 3D CT data sets without having to move the patient between separate imaging systems.

SUMMARY

According to some embodiments of the invention, a multimodal system for breast imaging includes an x-ray source and an x-ray detector configured to detect x-rays from the x-ray source after passing through at least a portion of a breast. The multimodal system includes an x-ray detector translation system operatively connected to the x-ray detector so as to be able to translate the x-ray detector from a first displacement from the breast to a second displacement at least one of immediately adjacent to or in contact with the breast. The multimodal system includes an x-ray image processor configured to communicate with the x-ray detector so as to: receive a computed tomography (CT) data set from the x-ray detector, the CT data set being detected by the x-ray detector at the first displacement; compute a CT image of the breast based on the CT data set; receive a mammography data set from the x-ray detector, the mammography data set being detected by the x-ray detector at the second displacement; and compute a mammography image of the breast based on the mammography data set.

According to some embodiments of the invention, a method for performing multimodal breast imaging includes obtaining a CT data set from an x-ray detector at a first displacement from a breast, and computing a CT image of the breast based on the CT data set. The method also includes obtaining a mammography data set from the x-ray detector at a second displacement at least one of immediately adjacent to or in contact with the breast, and computing a mammography image of the breast based on the mammography data set.

BRIEF DESCRIPTION OF THE DRAWINGS

Further objectives and advantages will become apparent from a consideration of the description, drawings, and examples.

FIG. 1A shows the system in the configuration for breast computed tomography (CT), with the x-ray beam emerging from the x-ray source, passing through an x-ray collimator, passing through the breast, and striking the detector. The system is capable of complete (greater than 360°) rotation around the breast to acquire the breast CT data. The x-ray source is positioned from the axis of rotation by the source to isocenter distance (SIC), and the distance between isocenter and the x-ray detector is defined as the detector to isocenter distance (DIC).

FIG. 1B shows the system in the configuration for breast CT, with the x-ray tube support and detector support resting upon a rotating gantry. The gantry rotates around the isocenter, which is defined by the bearing system, and is propelled by the motor, which is often a part of the bearing system.

FIG. 2A illustrates the geometry for breast CT acquisition, while FIG. 2B illustrates the geometry for 2D mammography acquisition, where the x-ray tube and associated support structures are translated along the gantry towards the breast, to reduce the DIC. This geometry is similar to that of digital mammography.

In FIG. 4B, the entire gantry has been translated relative to its mounting bracket on the gantry motor assembly. This geometry keeps the same source to detector distance for 2D mammography acquisition as is used for 3D breast CT acquisition. In this configuration, the x-ray tube support and detector support structures do not necessarily translate on top of the gantry; rather the gantry translates relative to the motor assembly.

DETAILED DESCRIPTION

Figure 1A:
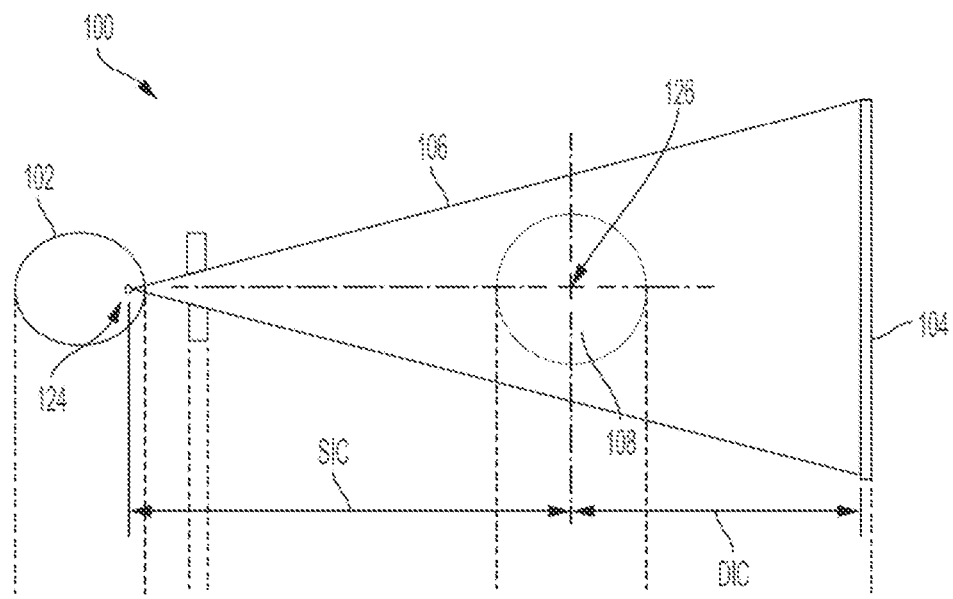
FIG. 1A is a schematic illustration of a top view of a multimodal system for breast imaging according to some embodiments of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The introduction of tomosynthesis to the field of breast imaging was largely enabled by the fact that it was coupled to existing digital mammography systems. This observation is critical, because it was widely appreciated that digital mammography systems excel at microcalcification detection, while the early tomosynthesis systems would likely be more appropriate for mass lesion detection—indeed, it was recognized that tomosynthesis would not be as efficient as digital mammography for microcalcification detection. Thus, the early introduction of tomosynthesis into the US market (i.e., FDA approval) required that it be an add-on to mammography, and not a standalone breast imaging modality.

Embodiments of the current invention utilize mammography's high resolution capabilities as well as the pseudo-3D image acquisition functionality provided by tomosynthesis. The invention according to some embodiments includes a single breast imaging system which allows the acquisition of a 2D conventional mammogram, with the breast in near-contact to the detector, and then enables quick repositioning (and potential reconfiguring) for the acquisition of 3D breast CT data sets.

In addition, because of the need to produce high-quality images close to the chest wall, the cone beam geometry used for breast CT systems is typically a half cone beam geometry where the x-ray focal spot is positioned towards the posterior side of the breast. This geometry creates a large cone angle, which is largest towards the anterior part of the breast. Because large cone angle imaging suffers from a null cone due to the violation of Tuy's principle, embodiments of the current invention also include the potential of including multiple x-ray focal spots within a single vacuum enclosure, to span the anterior-posterior (A-P) distance and create a number of projection images which have reduced cone angle.

Embodiments of the current invention enable high-quality two-dimensional digital mammography acquisition, on a fully three-dimensional (greater than 360° angular acquisition) breast computed tomography imaging system (bCT). The system may or may not also have the ability to do limited angle tomography (also known as tomosynthesis), for example with acquisition angles ranging from 15° to 60° in total angulation.

While breast CT has been shown to deliver superior mass lesion detection performance compared to digital mammography, many factors including spatial resolution, image noise, focal spot blur, etc., combine to reduce the detectability of microcalcifications in a fully 3D computed tomography image data set of the breast. While many research groups are working to address these limitations, embodiments of the current invention combine a digital mammography system enabling the acquisition of one or more digital mammograms of the breast in the same setting as the acquisition of a fully 3D breast CT data set.

Furthermore, in some embodiments, the bCT system can be a cone beam bCT system. While the cone beam CT geometry used for imaging the breast has been relatively robust against artifacts produced by the cone beam geometry, the role of these cone beam artifacts may not be fully appreciated by the research imaging community. Thus, embodiments of the current invention can also include the introduction of multisource x-ray tube technology which directly addresses the limitations of cone beam CT geometry. One configuration of multisource x-ray tube technology is defined here as "overlapping x-ray beam geometry."

Figure 1B:
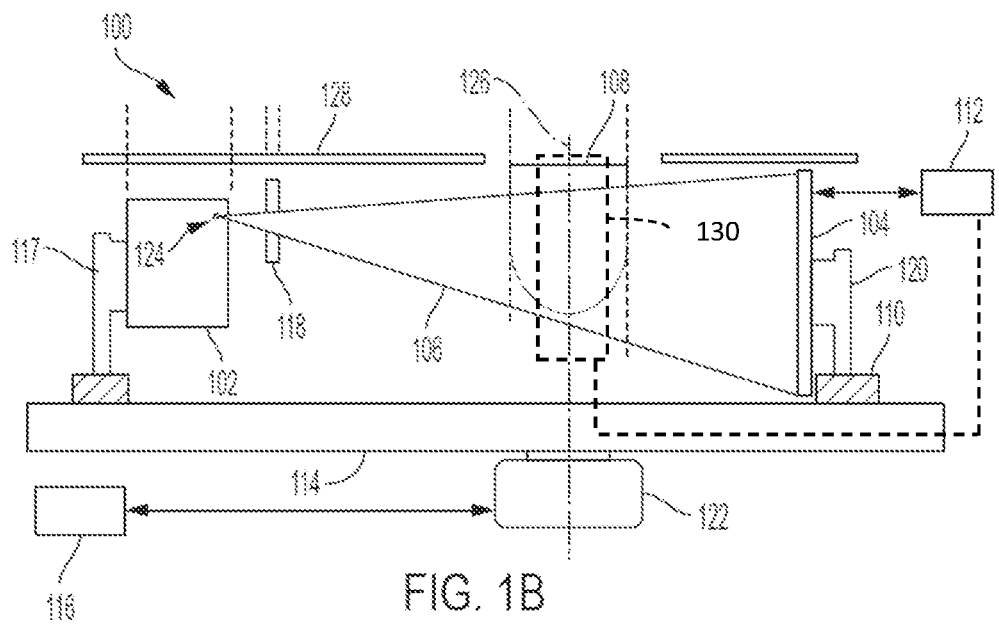
FIG. 1B is a schematic illustration of a side view of a multimodal system for breast imaging according to some embodiments of the current invention.

FIGS. 1A and 1B are schematic illustrations of a multimodal system 100 for breast imaging according to some embodiments of the current invention. FIG. 1A illustrates a top view and FIG. 1B illustrates a side view of the system 100. The multimodal system 100 according to some embodiments includes an x-ray source 102, and an x-ray detector 104 configured to detect x-rays 106 from the x-ray source 102 after passing through at least a portion of a breast 108. The system 100 includes an x-ray detector translation system 110 operatively connected to the x-ray detector 104 so as to be able to translate the x-ray detector 104 from a first displacement from the breast 108 to a second displacement at least one of immediately adjacent to or in contact with the breast 108. The system 100 includes an x-ray image processor 112 configured to communicate with the x-ray detector 104 so as to receive a CT data set from the x-ray detector 104, the CT data set being detected by the x-ray detector 104 at the first displacement, and compute a CT image of the breast 108 based on the CT data set. The x-ray image processor 112 is further configured to communicate with the x-ray detector 104 so as to receive a mammography data set from the x-ray detector 104, the mammography data set being detected by the x-ray detector 104 at the second displacement, and compute a mammography image of the breast 108 based on the mammography data set.

The multimodal system 100 according to some embodiments includes a gantry 114 mechanically coupled to the x-ray source 102 and the x-ray detector 104, and a gantry controller 116. The gantry controller 116 is configured to control the gantry 114 to rotate the x-ray source 102 and the x-ray detector 104 around the breast 108 during detection of the CT data set, and prevent the gantry 114 from rotating when the x-ray detector 104 is at the second displacement.

The multimodal system 100 according to some embodiments includes an x-ray source support 117, and an x-ray collimator 118 that collimates the x-rays emitted by the x-ray source 102. The x-rays are focused on the breast 108 at the x-ray focal spot 124. The multimodal system 100 may also include a detector support 120. The detector support 120 may operatively connect the x-ray detector 104 to the x-ray detector translation system 110.

The multimodal system 100 according to some embodiments includes a bearing and motor 122. The bearing and motor 122 rotate the gantry 114 around the axis of rotation 126. The gantry 114 may be positioned under a patient table 128. The patient's breast 108 may hang pendant through a hole in the patient table 128 during imaging of the breast 108. According to some embodiments, the x-ray source support 117 and the detector support 120 are configured to be translated towards and away from the isocenter of the gantry 114, which is defined as the axis of rotation 126 extending through the breast 108. According to some embodiments, the x-ray source 102 is a cone beam x-ray source and the x-ray detector 104 is a flat panel x-ray detector, such that the multimodal system 100 can produce a cone-beam CT data set and perform cone beam CT imaging.

FIGS. 2A-6B show a multimodal system according to various embodiments of the present invention. Like reference numerals as in FIGS. 1A and 1B correspond to like features. For example reference numerals 104 in FIG. 1A, 204 in FIG. 2A, and 304 in FIG. 3A each refer to the x-ray detector.

Figure 2A:
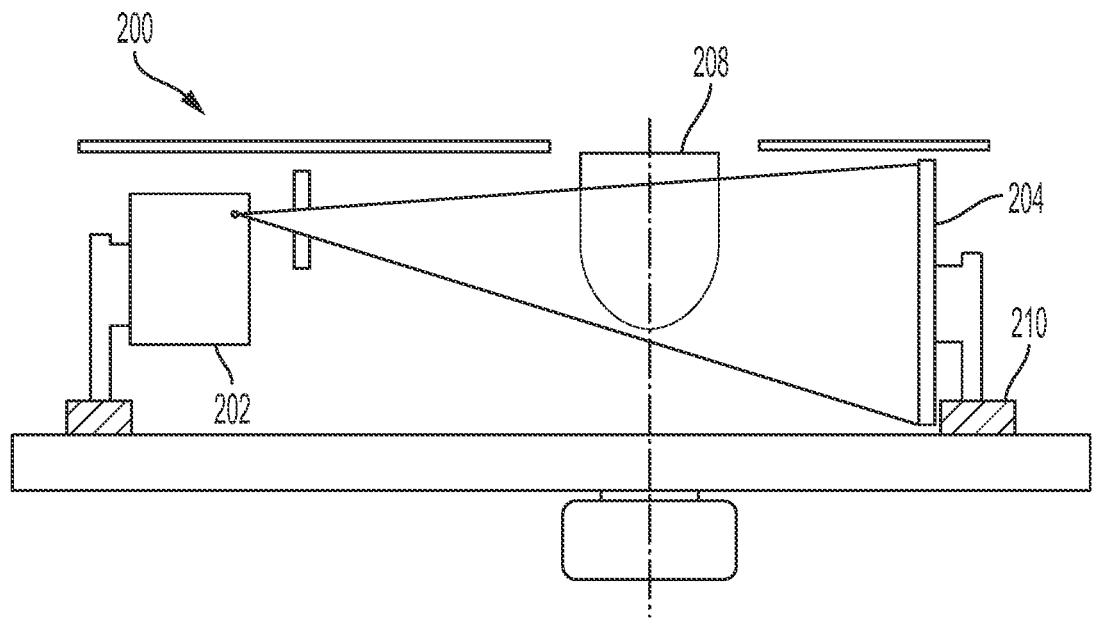
FIGS. 2A and 2B are schematic illustrations of a multimodal system enabling repositioning of the x-ray detector according to some embodiments of the current invention.
Figure 2B:
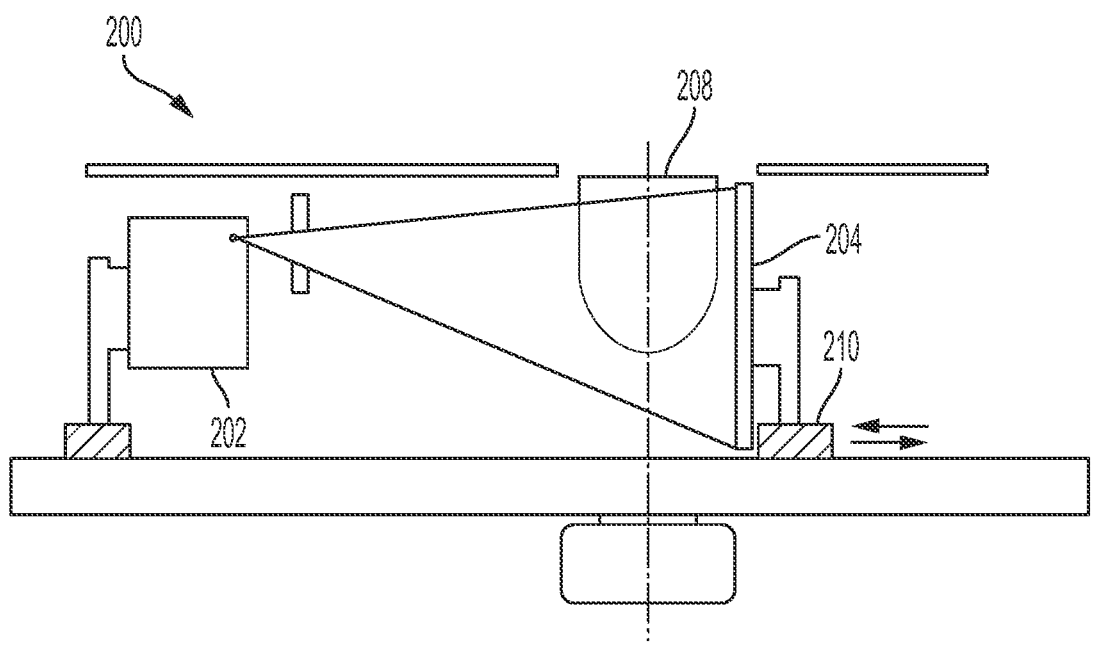

FIGS. 2A and 2B are schematic illustrations of a multimodal system 200 enabling repositioning of the x-ray detector 204 according to some embodiments of the current invention. FIG. 2A shows the x-ray detector 204 at a first displacement from the breast 208. FIG. 2B shows the x-ray detector 204 at a second displacement at least one of immediately adjacent to or in contact with the breast 208. The x-ray detector translation system 210 translates the x-ray detector 204 from the first position shown in FIG. 2A to the second position shown in FIG. 2B. The x-ray detector translation system 210 according to some embodiments is configured to translate the x-ray detector 204 from the first displacement to the second displacement without changing a position of the x-ray source 202, as illustrated in FIGS. 2A and 2B.

The system 200 in FIG. 2A shows the breast CT system is configured for CT imaging, while FIG. 2B illustrates the system 200 with the x-ray detector 204 moved towards the isocenter by mechanical translation of the x-ray detector 204. The process of moving the x-ray detector 204 closer to the breast 208 reduces the magnification of the breast 208 and reduces the consequences of the finite size of the focal spot—increasing spatial resolution. In practice, using conventional x-ray source and detector technology to produce a digital mammogram may also include the reduction of the x-ray source potential to that similar of digital mammography, for example, 26-35 kV, and changing the mode of the detector acquisition to a 1×1 mode. This may improve the spatial resolution of the detector to be similar to that used for conventional digital mammography.

It is noted that often a 2×2 mode of detector element binning is used to increase the frame rate of the detector necessary for breast CT acquisition. Current technology examples of this include that of the Varian PAXSCAN 4030CB detector, which has 194 µm native detector elements side-length in 1×1 mode with an acquisition rate of 7.5 frames per second, and 388 µm effective detector elements in a 2×2 mode with 30 frames per second. Another example is that of the DEXELA 2329 detector, which has 75 µm native detector elements side length in 1×1 mode (at 26 frames per second), and 150 µm effective detector element size at 2×2 acquisition mode (with approximately 50 frames per second). These cone beam detector systems demonstrate flexibility, with the ability to trade-off spatial resolution for temporal resolution, and vice versa. Embodiments of the current invention capitalize on this ability, using the high spatial resolution (low temporal resolution) mode of acquisition for digital mammography, and the higher temporal resolution (lower spatial resolution) mode of acquisition for breast CT.

Figure 3A:
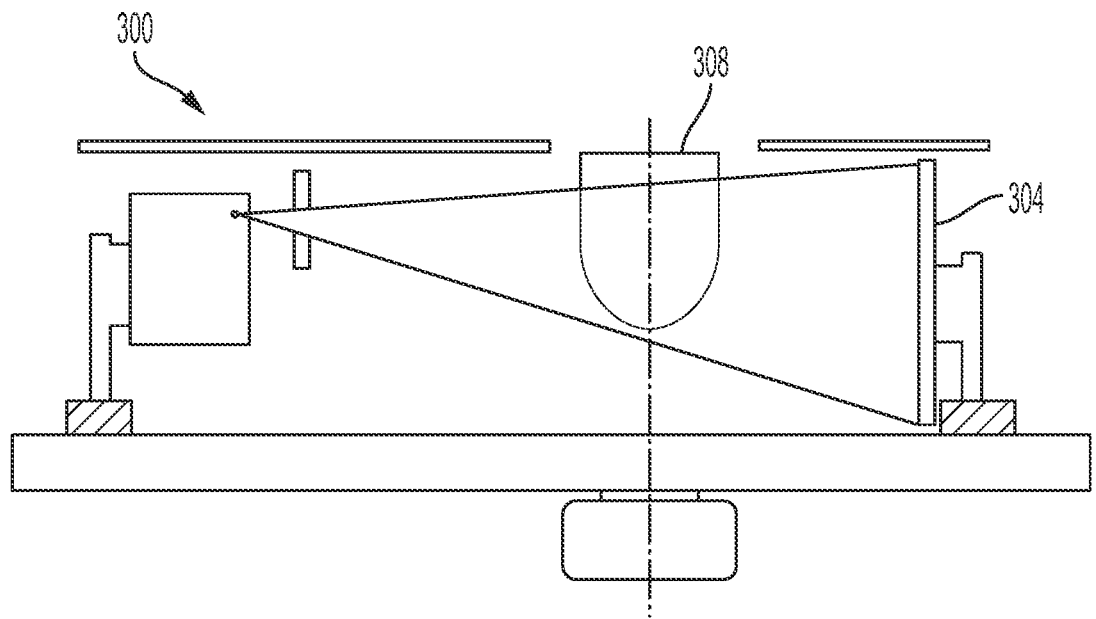
FIGS. 3A and 3B illustrate the introduction of an anti-scatter x-ray grid when the system is used in digital mammography acquisition mode, to reduce the scatter in this acquisition geometry. The x-ray scatter grid can be mechanically translated into the x-ray field prior to the acquisition of the digital mammogram.
Figure 3B:
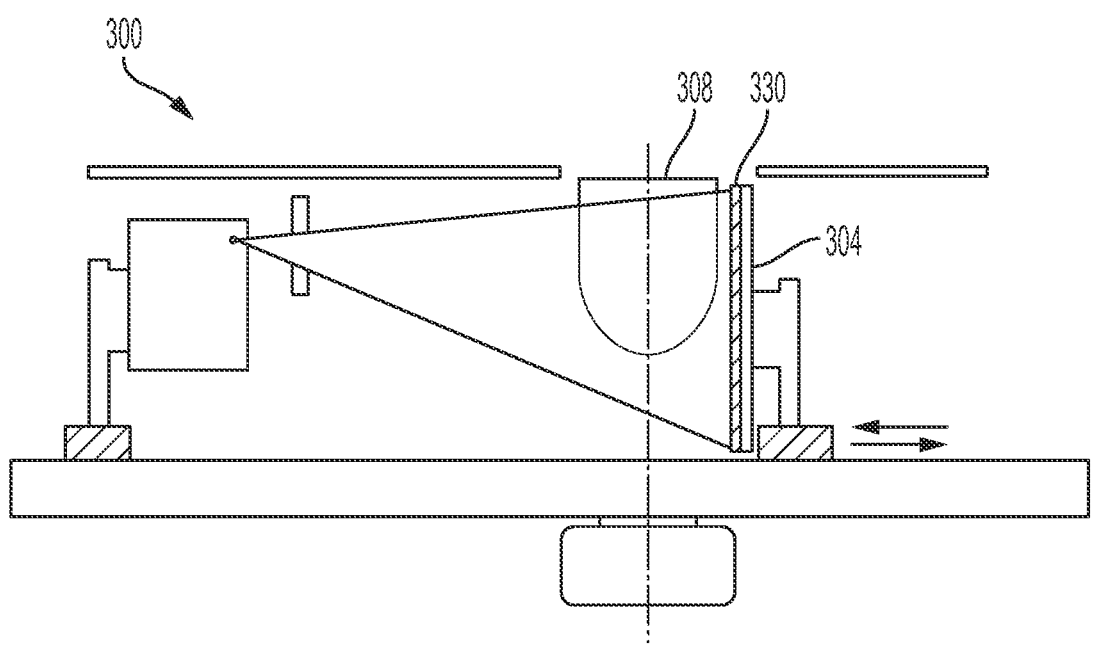

FIGS. 3A and 3B illustrate the introduction of an anti-scatter x-ray grid 330 when the system is used in digital mammography acquisition mode, to reduce the scatter in this acquisition geometry. This is largely mandated because in FIG. 3B the x-ray detector 304 has been moved to the proximity of the breast 308, and therefore more x-ray scatter will be detected due to solid angle considerations. The configuration shown in FIG. 3B illustrates an anti-scatter x-ray grid 330, which can be moved through automatic translation either in or out of the x-ray beam. For example, anti-scatter x-ray grid 330 could be coupled to a computer-controlled actuator, enabling a user to remotely control the insertion and removal of the anti-scatter x-ray grid 330.

It is noted that previous research has suggested that the use of the traditional x-ray scatter grids for digital mammography is only advantageous for larger compressed breast thicknesses (for example, greater than 5 cm compressed breast thickness) and may not be necessary for smaller breasts. FIG. 3A shows the x-ray detector 304 in a position for CT imaging, and the anti-scatter x-ray grid 330 is not used. In FIG. 3B, the x-ray detector 304 is positioned for mammography imaging, and an anti-scatter x-ray grid 330 is used. The ability to move the anti-scatter x-ray grid 330 in and out of the beam under computer control mechanical translation allows it to be used in the most optimal setting.

Figure 4A:
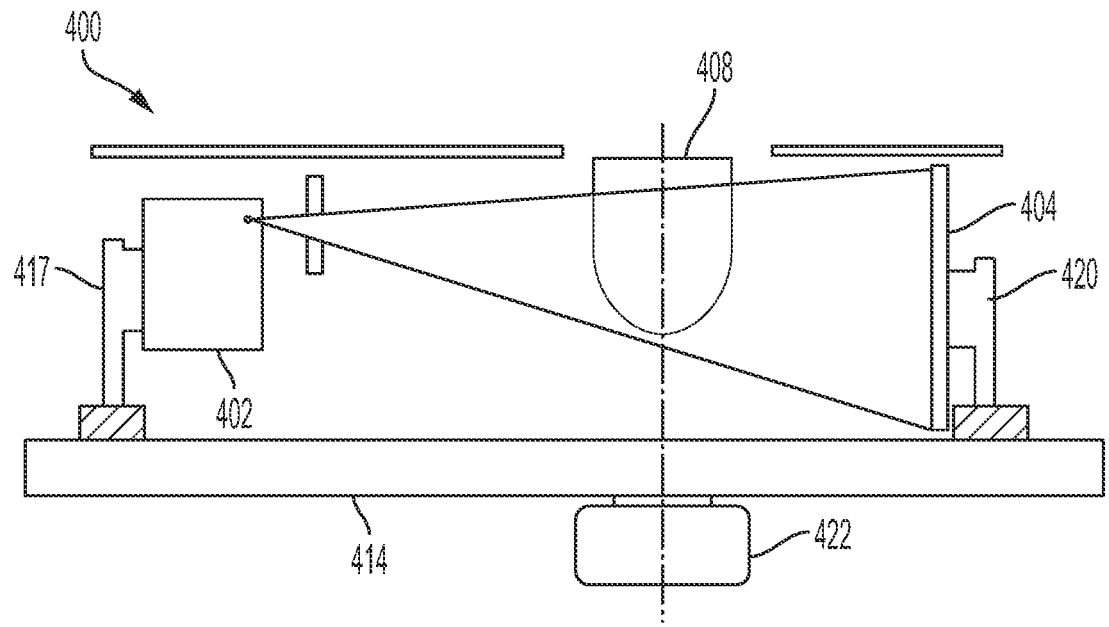
FIGS. 4A and 4B illustrate the translation of the x-ray detector according to some embodiments of the invention.
Figure 4B:
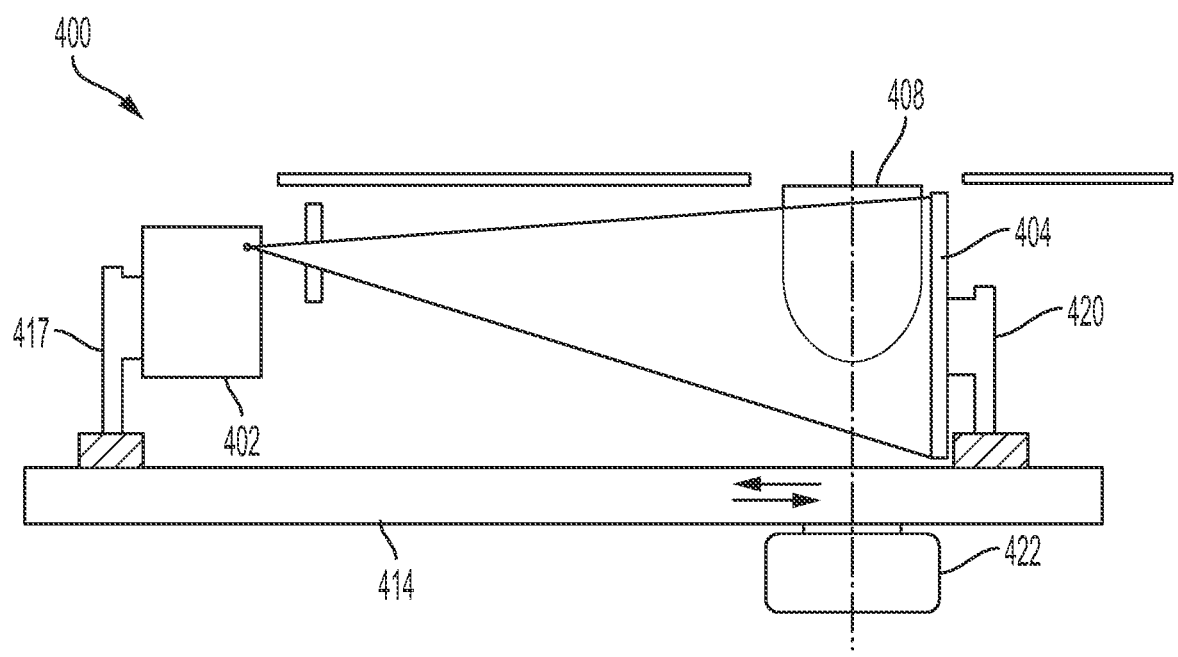

FIGS. 4A and 4B illustrate the translation of the x-ray detector 404 according to some embodiments of the invention. FIG. 4B is shown to contrast with the geometry shown in FIG. 4A. In this embodiment, the x-ray source support 417 and the x-ray detector support 420 remain static on the gantry 414, and the entire gantry 414 is translated such that the x-ray detector 404 becomes closer to the breast 408 (which is at the isocenter of the scanner), while the x-ray source 402 becomes further away from the breast. The bearing and motor 422 may serve as the x-ray detector translation system in some embodiments, both rotating and translating the gantry 414. Alternatively, the bearing and motor 422 may rotate the gantry 414, and an additional x-ray detector translation system (e.g., a motor and ball drive, not shown) may be provided that translates the gantry 414. The x-ray detector translation system of some embodiments translates the x-ray source 402 in order to maintain a same distance between the x-ray source 402 and the x-ray detector 404 when the x-ray detector 404 is at the first displacement (FIG. 4A) and at the second displacement (FIG. 4B).

The geometry shown in FIG. 4B has less focal spot magnification than the geometry depicted in FIG. 2B. The reduced focal spot magnification increases spatial resolution by reducing the resolution losses from focal spot magnification. While this configuration may be advantageous from a mammography imaging standpoint, it also means that the CT gantry protrudes significantly from its central location in the geometry of the breast CT scanner. This may mean that the system cannot rotate over large angles while the x-ray gantry is positioned in the geometry shown in FIG. 4B.

It is noted that the geometry of FIG. 4B also allows, within the constraints of the geometry of the breast CT housing, for the system to acquire tomosynthesis images of the breast in addition to acquiring a digital mammogram of the breast. While tomosynthesis likely is not competitive with breast CT and therefore may not be needed in most circumstances, in some circumstances radiologists or other imaging professionals may want to compare tomosynthesis images with those of previous acquisitions, and in such case tomosynthesis images would be useful for these comparisons.

Figure 5A:
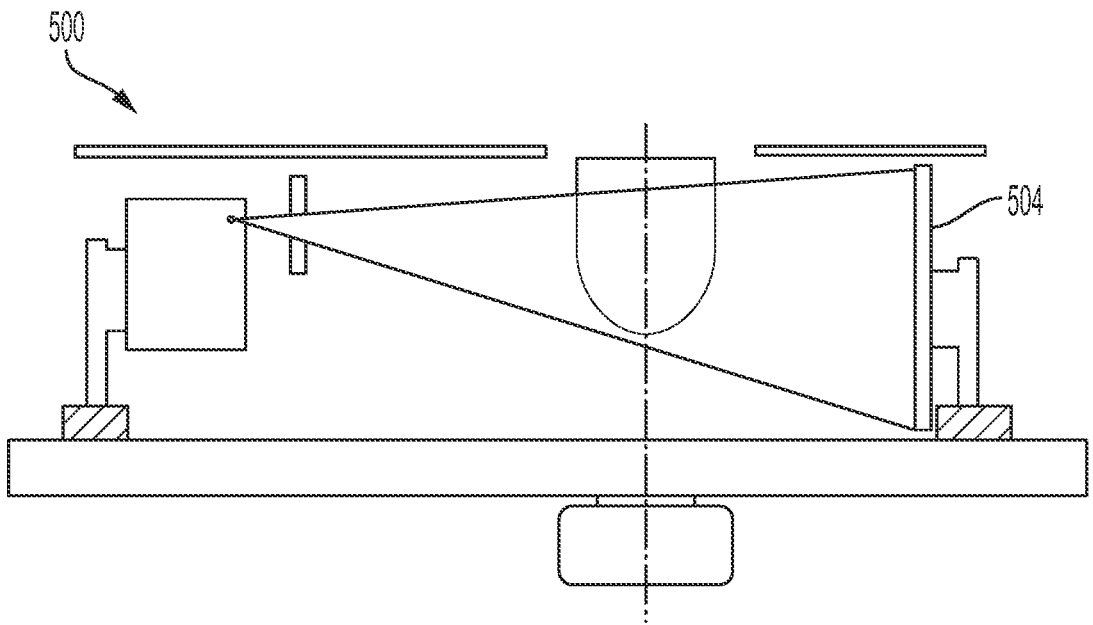
FIG. 5A shows a CT acquisition geometry.
Figure 5B:
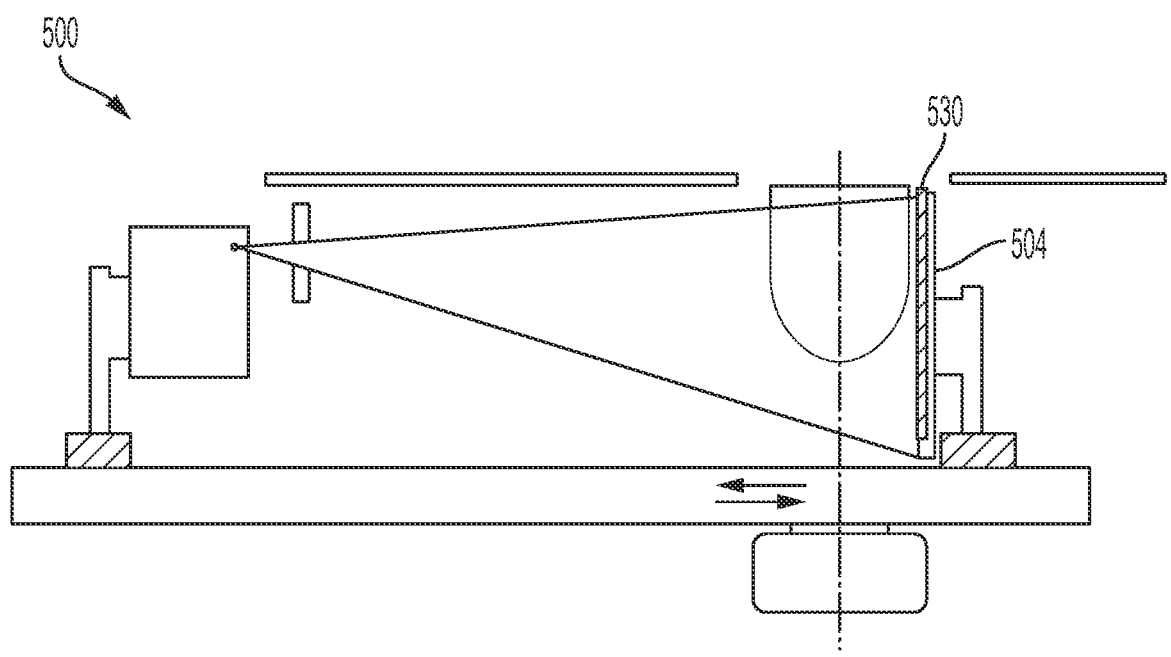
FIG. 5B shows the mammography and tomosynthesis acquisition modes with the gantry translation geometry, coupled with the anti-scatter x-ray grid according to some embodiments of the invention.

FIG. 5A shows a CT acquisition geometry, and FIG. 5B shows the mammography and tomosynthesis acquisition modes with the gantry translation geometry, coupled with the anti-scatter x-ray grid 530 according to some embodiments of the invention. As noted previously, the anti-scatter x-ray grid 530 could be deployed by motorized translation under computer control, to allow its use for imaging conditions where an anti-scatter x-ray grid would be beneficial.

According to some embodiments of the invention, the multimodal system further includes a breast immobilization device. The breast immobilization device is configured to immobilize the breast during detection of at least one of the CT data set and the mammography data set. Whereas the geometry of breast CT may be optimal with a cylindrical shape breast, for digital mammography and digital tomo synthesis, a compressed breast is a more desired shape.

Figure 6A:
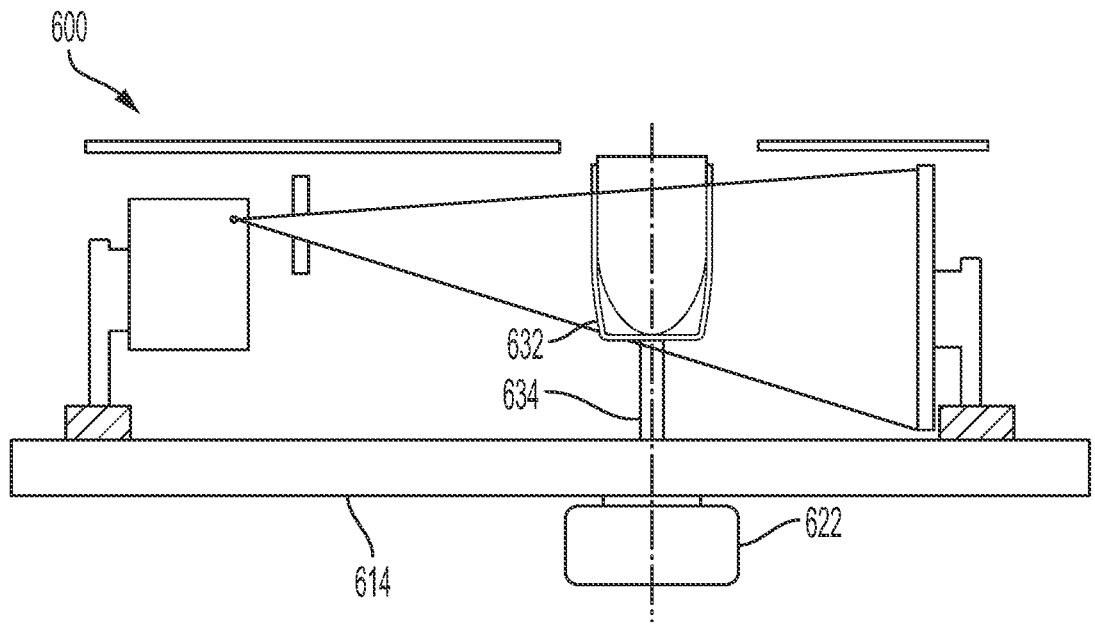
FIG. 6A illustrates the introduction of an immobilization device, which may also serve to compress the breast, and which can be used in the breast CT acquisition mode of the system. The compression/immobilization system can be supported from a stationary structural member which penetrates the rotating gantry and bearing assembly, or it can also be suspended from the patient table, which is also stationary with respect to the patient's breast.
Figure 6B:
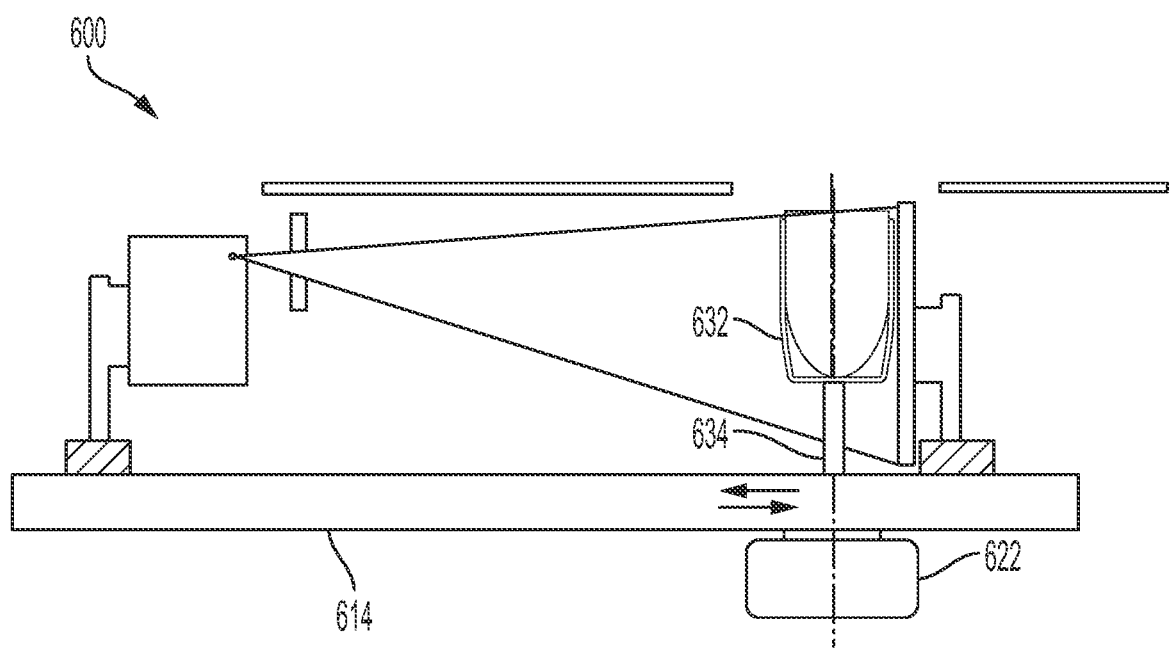
FIG. 6B is a schematic illustration of the breast compression/immobilization system deployed by the system in the geometry for acquisition of a digital mammogram. The system can be deployed with or without the x-ray scatter grid, as shown in FIGS. 3B and 4B. This figure shows the mammography geometry where the x-ray tube support and x-ray detector support for stationary relative to the gantry, and the gantry translates on the motor assembly. Another embodiment would include the translation of the x-ray detector system on the gantry to achieve a mammography geometry, as illustrated in FIG. 2B.

FIGS. 6A and 6B illustrate the use of an immobilization device 632, which may also serve to compress the breast. The mechanics of breast compression also serve to perform breast immobilization as well. Whereas breast compression is considered desirable from an imaging standpoint, immobilization is necessary to reduce patient motion, and also to prevent the breast from moving during breast biopsy. The breast immobilization device includes a radiolucent material in some embodiments, which defines a window permitting a biopsy needle to pass therethrough. In some embodiments, the biopsy window is a cut-out gap.

The breast immobilization device 632 shown in FIGS. 6A and 6B is mounted on a datum surface which does not rotate (or under most circumstances, translate) with the gantry 614. The breast immobilization device 632 according to some embodiments is attached to a stationary post 634 which is mounted on the base of the imaging system but penetrates through a central hole in the motor assembly and gantry 614. It is noted that with respect to penetrating the gantry 614, for the embodiment where the gantry 614 translates across the bearing and motor 622, the stationary post 634 may be placed within a slot in the translating gantry 614.

As an alternative embodiment for configuring the compression/immobilization device, it is possible to use the patient table as the datum surface for mounting it. In such a case, the device may hang underneath it patient table. This may be useful when the table is capable of horizontal translation or vertical translation.

Figure 7:
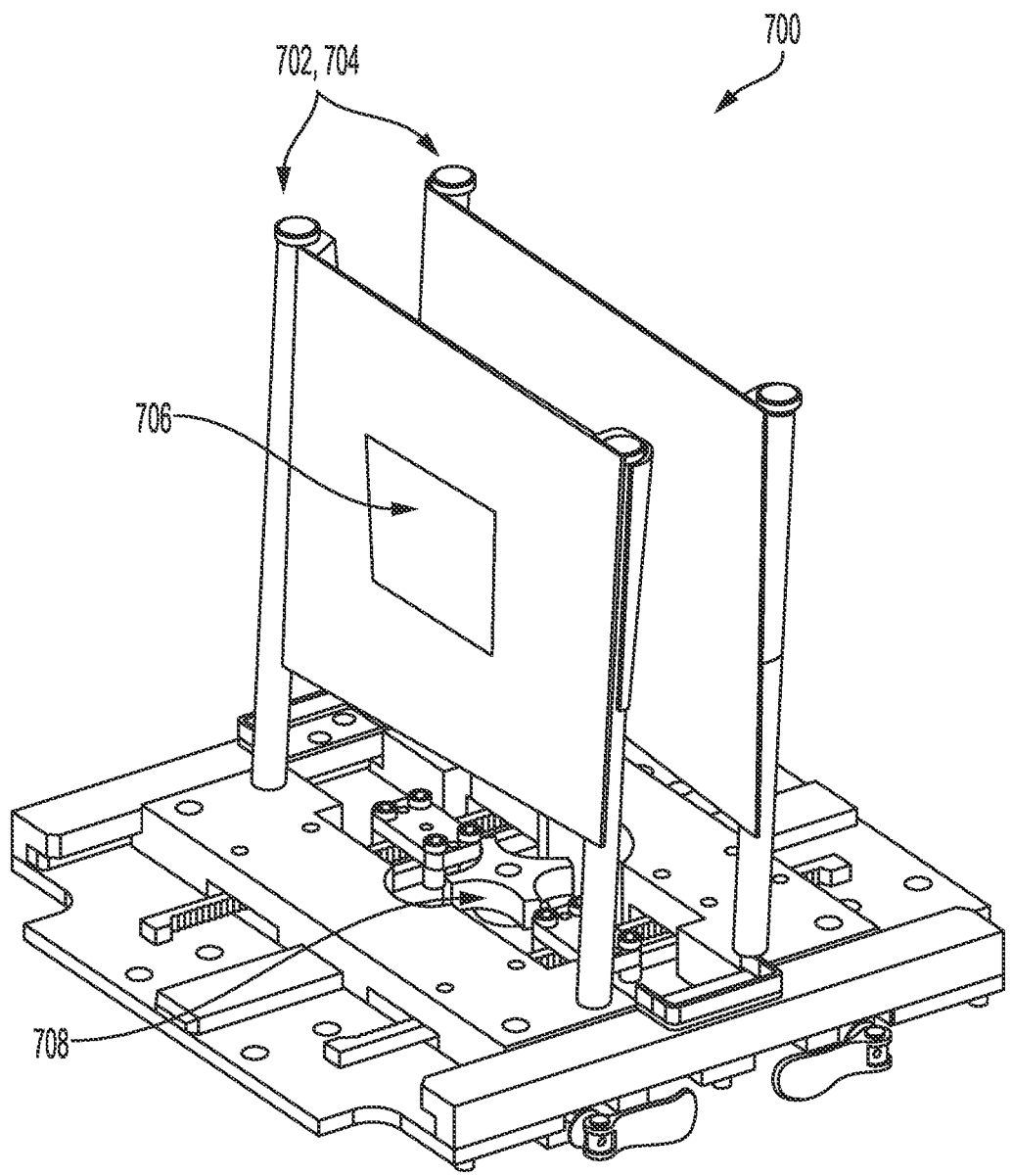
FIG. 7 is a schematic illustration of a remotely controlled compression/immobilization device with planar compression surfaces. One or both of the surfaces may also provide a biopsy access window, as illustrated.

The experience with compression during digital mammography is widespread, and typically two planar services are used to achieve compression and immobilization. The base of the imaging platform typically serves as the bottom of the breast platform, and a panel which translates perpendicular to the plane of the surface of the breast imaging platform is used to apply compression/immobilization. Although two planar flat surfaces are often used for compression/immobilization in digital mammography, various levels of slight curvature and panel flex under spring tension have been used in clinical and commercial practice. FIG. 7 illustrates the use of a motor-controlled compression system 700 with planar compression surfaces 702, 704, which emulate the compression panels in current digital mammography and tomosynthesis systems. At least one of the compression panels 702, 704 may include a biopsy access window 706, enabling a biopsy needle to pass through the compression panel. The system 700 may include a screw that can be rotated manually or using a motor about the axis of rotation 708 to bring the planar compression surfaces 702, 704 closer to or farther away from one another.

Figure 8:
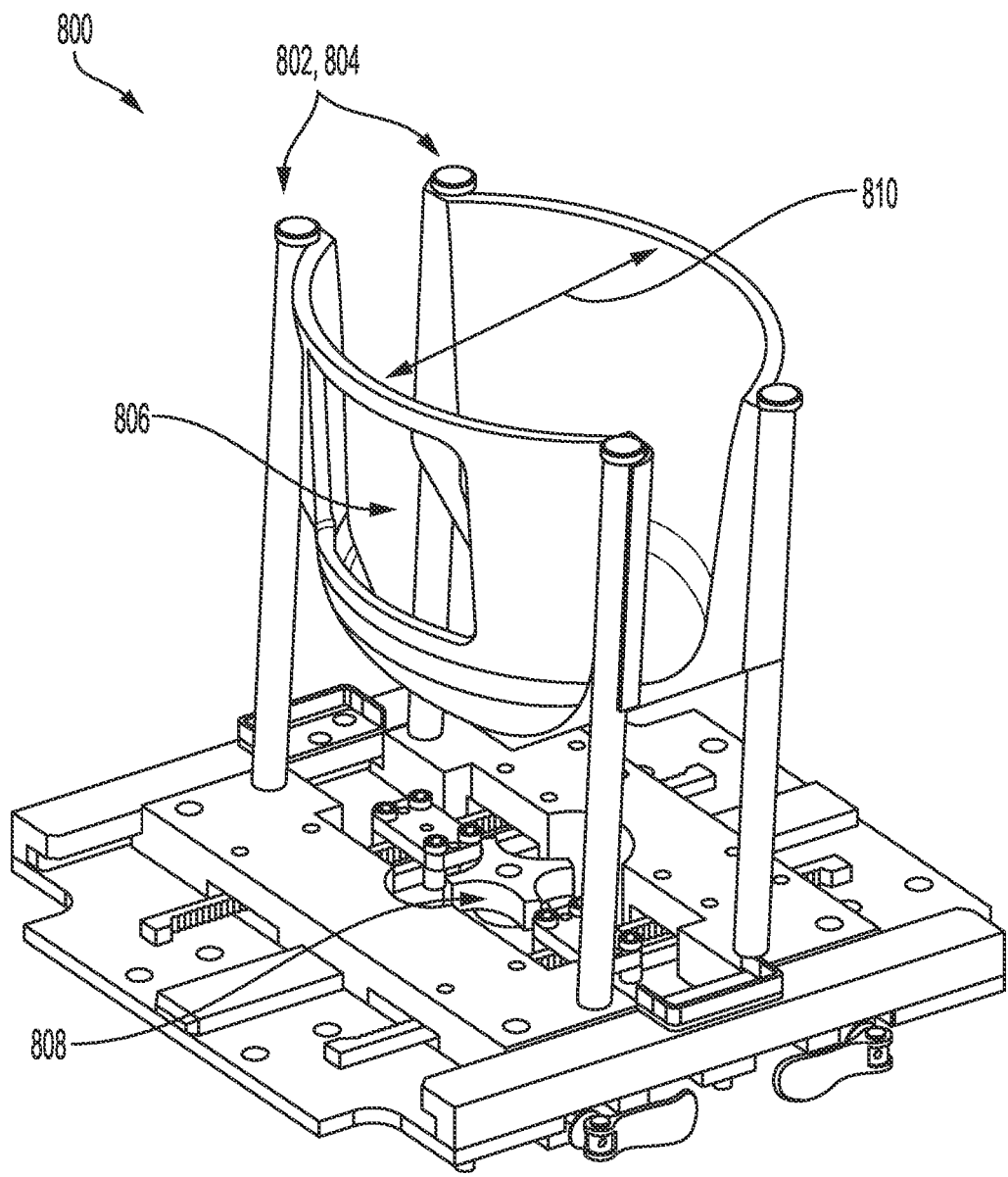
FIG. 8 is a schematic illustration of a remotely controlled compression/immobilization device with non-planar compression surfaces, which can be used to position the breast in a pseudo-cylindrical fashion, while maintaining superior immobilization for both imaging and biopsy.

FIG. 8 illustrates a non-planar compression system 800, which may be useful for breast CT acquisition, which generally images the breast in a more cylindrical shape, as opposed to the more flattened "pancake" shape of the breast in mammography. The non-planar compression system 800 includes two non-planar compression surfaces 802, 804. The two non-planar compression surfaces 802, 804 may be curved surfaces, for example, with the concave side of the curved surfaces facing one another. At least one of the compression panels 802, 804 may include a biopsy access window 806, enabling a biopsy needle to pass through the compression panel. The system 800 may include a screw that can be rotated manually or using a motor about the axis of rotation 808 to bring the non-planar compression surfaces 802, 804 closer to or farther away from one another. The non-planar compression surfaces 802, 804 may translate along the compression vector 810.

In some embodiments, the two surfaces 802 and 804 move towards a stationary center, so the breast is gradually compressed from both sides, and is not moved in either direction. This allows the breast to be centered appropriately in the FOV, and then compressed.

Figure 9:
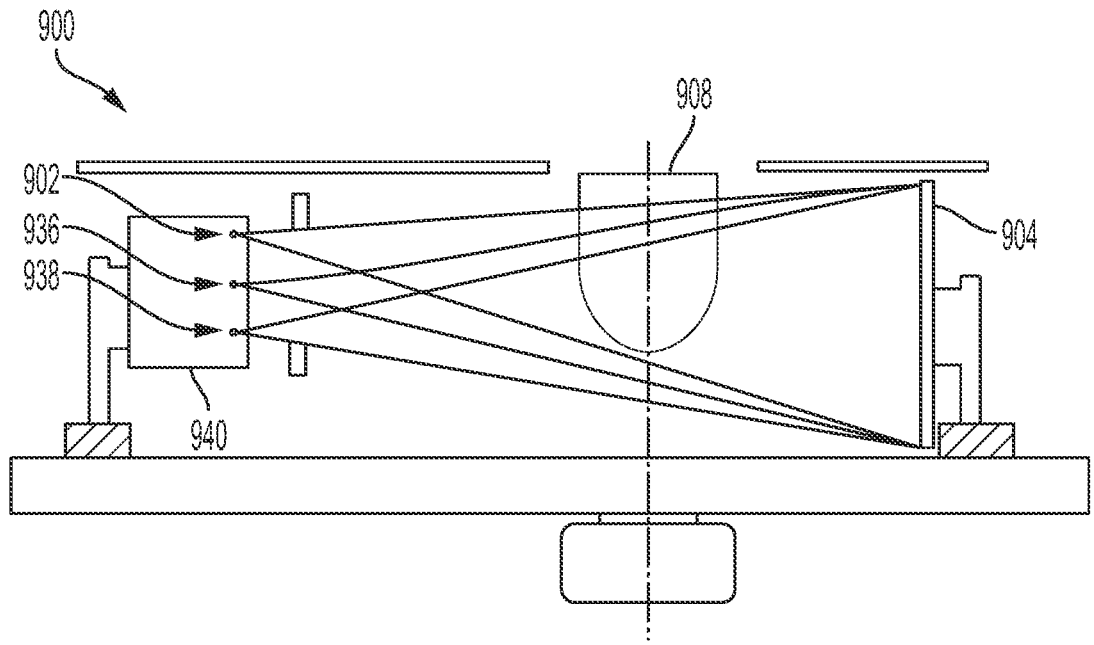
FIG. 9 is a schematic illustration of a breast CT system with an x-ray tube containing multiple focal spots, which are generally positioned along the z-axis of the imaging system—either colinearly or in a staggered position. The multiple focal spots enable CT acquisition with reduce cone angle, and in this configuration (referred to as overlapping geometry) each of the focal spots can be projected along most or all of the detector surface.

FIG. 9 is a schematic illustration of a multimodal system 900 that includes multiple x-ray sources 902, 936, 938 within a single vacuum x-ray tube enclosure 940. [5] This geometry shows overlapping fields where each source illuminates close to the entire x-ray detector 904 and covers a corresponding part of the breast 908. In principle, this geometry, which requires interleaved acquisition (from each source 902, 936, 938) by the x-ray detector 904, overcomes many of the aspects of the cone beam geometry used in breast CT.

Figure 10A:
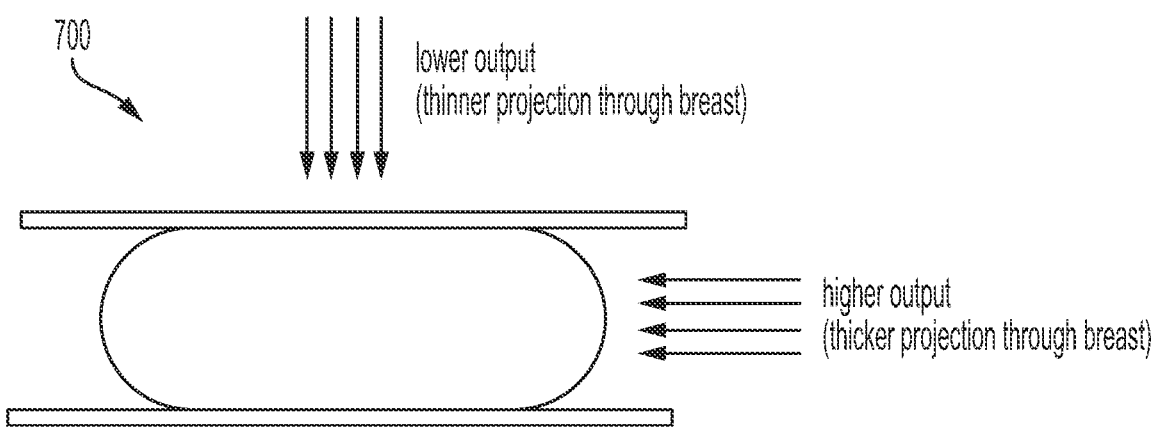
FIG. 10A is a schematic illustration demonstrating tube current modulation dedicated to breast CT for a compressed breast using a co-planar compression system.
Figure 10B:
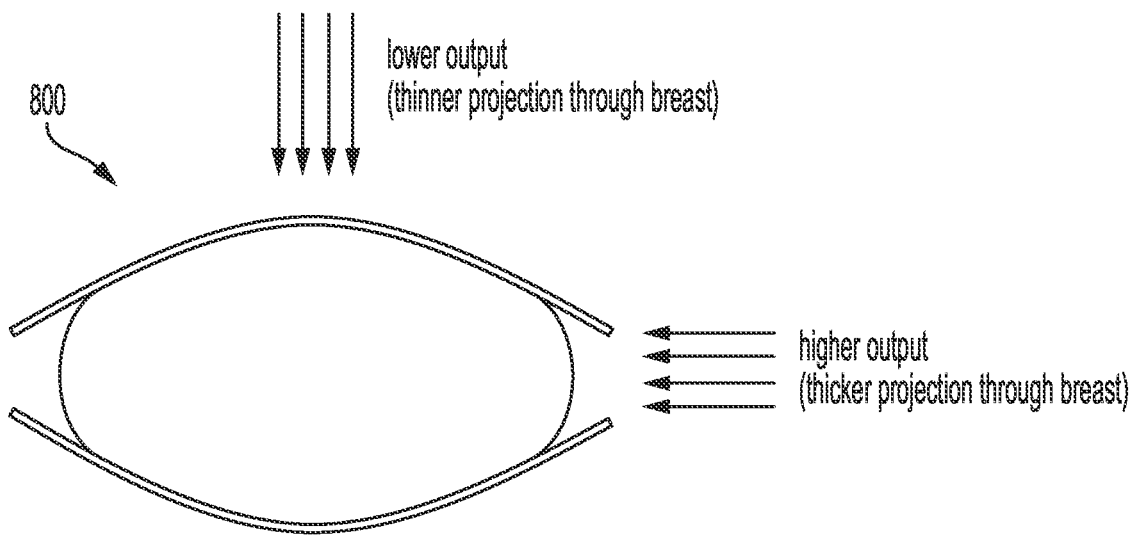
FIG. 10B is a schematic illustration demonstrating tube current modulation dedicated to breast CT for a breast which is compressed and immobilized using non-planar compression paddles.

FIG. 10A is a schematic illustration of breast compression using a planar compression system, such as the system 700 shown in FIG. 7. FIG. 10B is a schematic illustration of breast compression using a non-planar compression system, such as the system 800 shown in FIG. 8. To the extent that either the planar (FIG. 10A) or non-planar (FIG. 10B) compression surfaces manipulate the breast such that it is non-cylindrical, it is recognized that an elongated elliptical profile of the breast during breast CT may lend itself to tube current modulation techniques, which would increase the tube current (mA) to increase the x-ray flux to transmit through thicker sections of the breast, while reducing the x-ray flux (tube current) as the projection of the breast intersects the thinner cross-section of the breast under this compression scenario.

Figure 11:
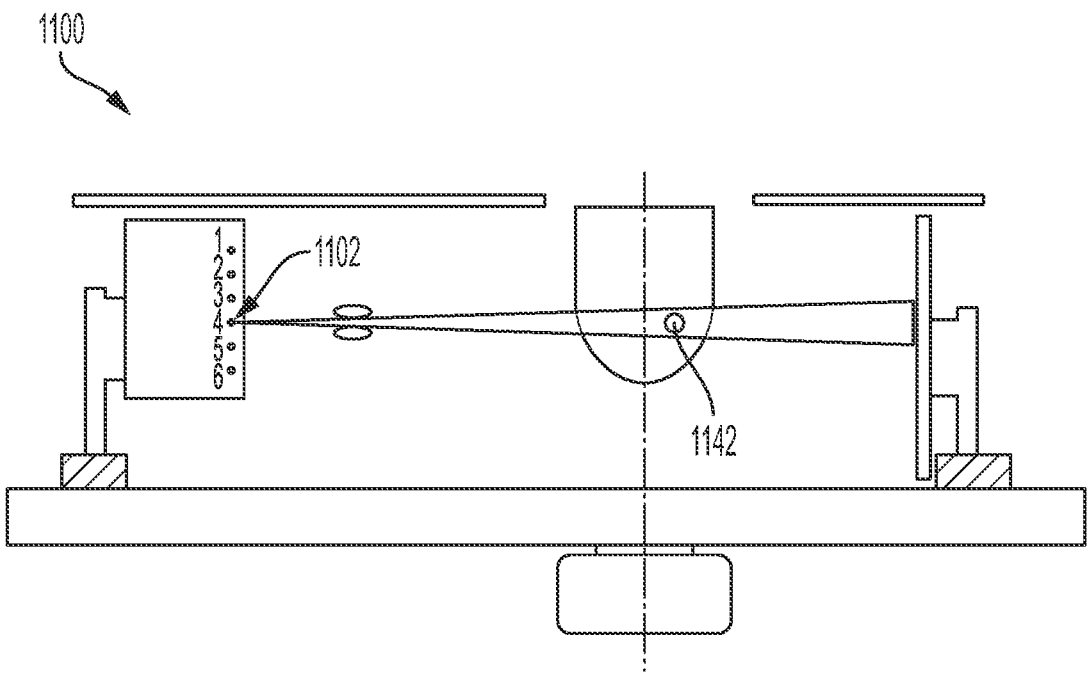
FIG. 11 is a schematic illustration of a multi-source system where only one (one or several, but not all) of the sources are used in imaging the location of a suspected lesion. This geometry allows the x-ray technique (mA or time or kV, or combinations of) to be increased to deliver higher signal-to-noise ratio (SNR) images, although the dose to the breast would be low because only a small fraction is irradiated. This geometry also virtually eliminates large cone angle, and could be used as a virtual (x-ray) image biopsy or this geometry could also be used to guide the physical needle-core (or other) biopsy of the breast.

FIG. 11 is a schematic illustration of a multimodal system 1100 that includes six x-ray sources. The multimodal system 1100 may be configured such that only one x-ray source 1102 (one or a subset) is fired during imaging. This x-ray source 1102 is located in the plane where a suspected lesion 1142 is known to exist, and therefore the x-ray source 1102 can be used to perform low-to-no cone angle scanning.

With a complete set of collimators for each source, in some embodiments, multiple x-ray sources with non-overlapping or overlapping projections onto the detector may be fired at the same time. For example, sources 1, 3, and 5 (odd sources) might be fired at one time point, and sources 2, 4, and 6 (even sources) would be fired simultaneously at another point in time. This firing sequence performed with stationary gantry provides scatter reduction for mammography, and such a sequence (odd, even, odd, even, . . . ) performed with gantry rotation during the acquisition of a breast CT data set would allow for full 3D reconstruction of the breast, with the virtual elimination of cone beam artifacts and the null cone (in Fourier space) that also accompanies cone beam acquisition. Such a pulsed system would also allow robust correction of scattered radiation in the projection images, as the tracts between the collimated primary beams would contain only the signal from scattered radiation.

According to some embodiments of the invention, the multimodal system may be configured to communicate with a robotic biopsy assembly. The x-ray image processor may be further configured to receive an indication from a user of a region of the breast to be biopsied based on the CT image and the mammography image, and control a robotic biopsy assembly to obtain tissue from the region. According to some embodiments, the multimodal system includes the robotic biopsy assembly.

Figure 12:
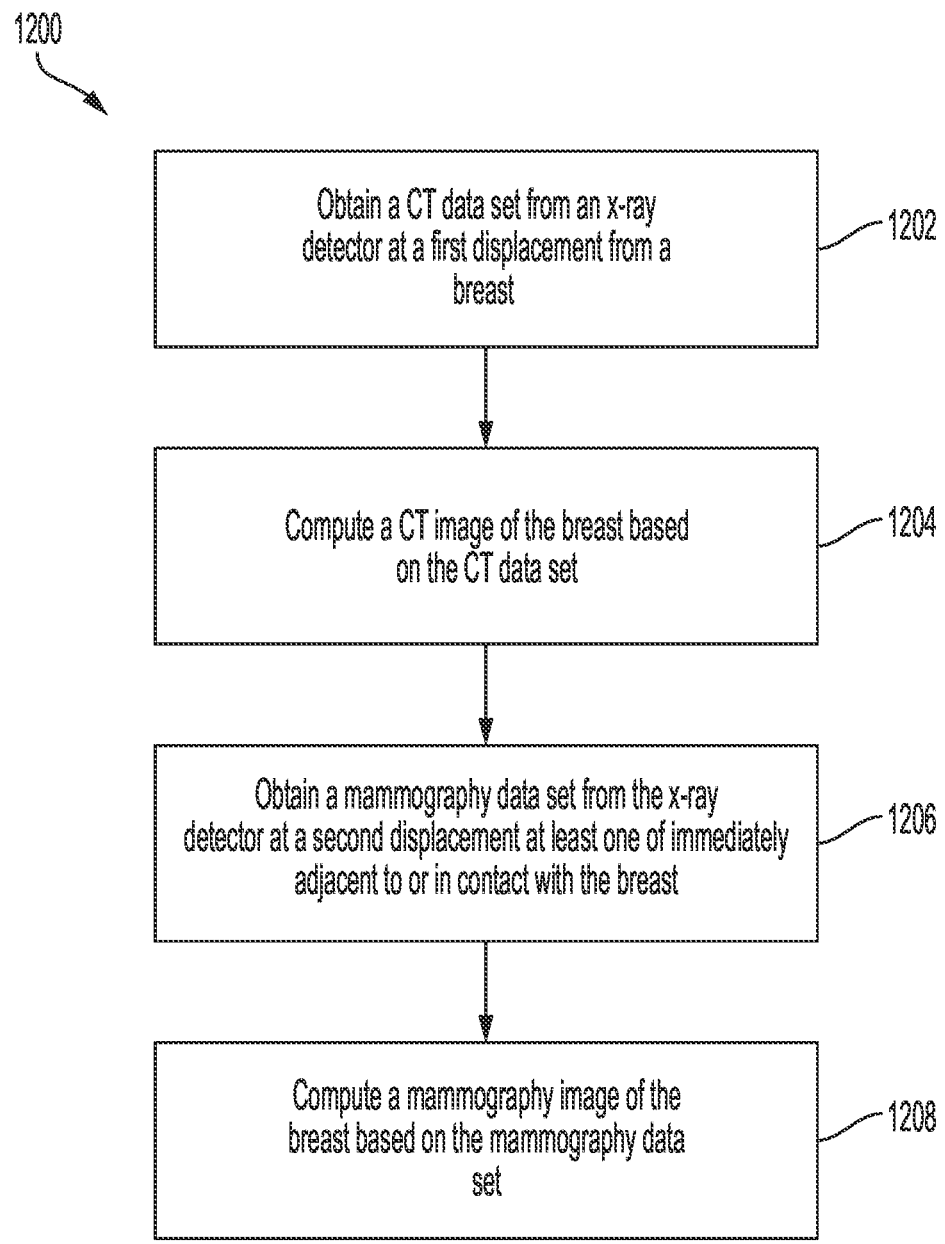
FIG. 12 is a flowchart that illustrates a method for performing multimodal breast imaging.

FIG. 12 is a flowchart that illustrates a method 1200 for performing multimodal breast imaging. The method 1200 includes obtaining a CT data set from an x-ray detector at a first displacement from a breast 1202, and computing a CT image of the breast based on the CT data set 1204. The first displacement allows full or partial rotation of the x-ray source and x-ray detector around the stationary breast. The method 1200 includes obtaining a mammography data set from the x-ray detector at a second displacement at least one of immediately adjacent to or in contact with the breast 1206, and computing a mammography image of the breast based on the mammography data set 1208. The second displacement allows limited x-ray tube rotation to allow acquisition of tomosynthesis data sets, with the breast and x-ray detector stationary.

According to some embodiments of the invention, the method 1200 further includes displaying the CT image and the mammography image of the breast. According to some embodiments, the method 1200 includes rotating the x-ray detector around the breast when the x-ray detector is at the first displacement, and preventing the x-ray detector from rotating around the breast when the x-ray detector is at the second displacement. This may prevent injury to the patient that may be caused if the detector were to rotate while in close proximity to the patient's breast.

According to some embodiments of the invention, the method 1200 includes receiving an indication from a user of a region of the breast to be biopsied based on the CT image and the mammography image and controlling a robotic biopsy assembly 130 (FIG. 1B) to obtain tissue from the region. Controlling the robotic biopsy assembly 130 to obtain tissue from the region may include positioning the robotic biopsy assembly 130 to obtain tissue from the region, the robotic biopsy assembly 130 including a biopsy needle; obtaining at least one of a second CT data set and a second mammography data set showing a position of the biopsy needle relative to the region; computing at least one of a second CT image and a second mammography image of the breast based on the at least one of a second CT data set and a second mammography data set; repositioning the robotic biopsy assembly 130 based on the at least one of a second CT image and a second mammography image; and controlling the robotic biopsy assembly 130 to obtain tissue from the region using the biopsy needle.

According to some embodiments of the invention, the method 1200 includes translating the x-ray detector from the first displacement to the second displacement without changing a position of an x-ray source providing x-rays detected by the x-ray detector. An example of this method is schematically illustrated in FIGS. 2A and 2B. According to some embodiments, the method 1200 includes translating the x-ray detector and an x-ray source providing x-rays detected by the x-ray detector in order to maintain a same distance between the x-ray source and the x-ray detector when the x-ray detector is at the first displacement and at the second displacement. An example of this method is schematically illustrated in FIGS. 4A and 4B.

According to some embodiments of the invention, translating the x-ray detector and the x-ray source comprises linearly translating a gantry physically coupled to the x-ray detector and the x-ray source, the gantry being configured to rotate the x-ray detector and the x-ray source around the breast when the x-ray detector is at the first displacement.

According to some embodiments of the invention, the method 1200 further includes immobilizing the breast during detection of at least one of the CT data set and the mammography data set using a breast immobilization device, the breast immobilization device comprising a radiolucent material defining a window permitting a biopsy needle to pass therethrough. According to some embodiments, the method 1200 includes receiving an indication from a user of a region of the breast to be biopsied based on the CT image and the mammography image; performing fluoroscopic imaging of the breast using the x-ray detector; and using the fluoroscopic imaging to control a robotic biopsy assembly 130 to obtain tissue from the region.

According to some embodiments of the invention, a multimodal system for performing computed tomography of a breast includes an x-ray source, a rotating gantry, and a detector to acquire projection images of the breast. The x-ray source may include one or more x-ray focal spots within a single enclosed vacuum housing.

The detector according to some embodiments is a flat panel detector, for example, using thin-film transistor or ceramic metal oxide semiconductor (CMOS) technology. The detector according to some embodiments is not flat. According to some embodiments, the detector uses at least two non-planar detector modules.

According to some embodiments of the invention, the multimodal system includes a gantry connected to the x-ray source and detector and configured to translate to place the detector close to the breast in order to acquire a digital mammogram. According to some embodiments, the detector is a digital detector that has detector elements no larger than 0.200 mm on the side.

According to some embodiments of the invention, the both the x-ray source and detector modules translate in unison, then become stationary, to acquire the digital mammogram. According to some embodiments, both or either of the x-ray source and the detector translate independently, and the two acquire the digital mammogram. According to some embodiments, the patient lies on a table which is horizontal. According to some embodiments, the patient table is not horizontal. According to some embodiments, the patient table is not a plane. According to some embodiments, the gantry rotation is less than 360°, equal to 360°, or greater than 360°. According to some embodiments, the gantry rotation is less than 180° but greater than 15°.

According to some embodiments, the system includes a compression device that immobilizes the breast for imaging. The compression device may use two planar structures to immobilize and compress the breast. Alternatively, the compression device may use two non-planar structures to immobilized and compress the breast. The system may use both types of compression device, for example, a planar compression device may be use for mammography imaging, which a non-planar compression device may be used for 3D CT imaging.

According to some embodiments, the breast is compressed, and a robotic device targets a region of the breast for biopsy which is identified by a medical professional using images acquired on the system. In some embodiments, the image guidance may be provided by breast CT images In some embodiments, the image guidance may be provided by one or more mammograms. In some embodiments, the image guidance is provided by tomosynthesis or limited angle tomography systems. The image guidance may be provided by multiple types of imaging.

According to some embodiments, the x-ray source and detector systems are used in a fluoroscopic acquisition mode for biopsy guidance and confirmation. According to some embodiments, a cone beam imaging system, for dedicated breast or other clinical applications, uses two or more x-ray sources configured along the z-axis to address the cone beam angle issues of breast CT geometry. According to some embodiments, several x-ray sources are pulsed simultaneously (during the same frame acquisition time) to acquire multiple x-ray projection images on a single flat or curved panel detector system.

According to some embodiments of the invention, one of the x-ray sources in an x-ray source array, as shown in FIG. 11, is used for the scan. A higher dose, higher SNR image of a suspected lesion at the appropriate location in the breast may be targeted by one x-ray source in the array, with higher technique factors (higher mA or higher kV or both) to produce higher quality images. The detector system may be set to a higher resolution mode such as 1×1 mode instead of 2×2 mode used for general cone beam imaging. The images may help in guiding a breast biopsy to the site of a suspected lesion.

REFERENCES

[1] Reese D F, Carney J A, Gisvold J J, Karsell P R, Kollins S A. 1976. Computerized reconstructive tomography applied to breast pathology. *Am. J. Roentegnol.* 126:406-12

[2] Boone J M, Nelson T R, Lindfors K K, Seibert J A. 2001. Dedicated breast C T: radiation dose and image quality evaluation. *Radiology* 221:657-77

[3] Chen B, Ning R. 2002. Cone-beam volume C T breast imaging: feasibility study. *Med. Phys.* 29:755-70.

[4] Becker A E, Hernandez A M, Boone J M, and Schwoebel P R, A Prototype Multi-X-ray Source Array (MXA) for digital breast tomosynthesis. Phys. Med. Biol. 65 235033.

[5] Becker A E, Hernandez A M, Schwoebel P R, and Boone J M, Cone Beam C T Multisource Configurations: Evaluating Image Quality, Scatter, and Dose Using Phantom Imaging and Monte Carlo Simulations. Phys. Med. Biol. 65 235032

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A multimodal system for breast imaging, comprising:
a gantry;
an x-ray source attached to said gantry;
an x-ray detector attached to said gantry and configured to detect x-rays from said x-ray source after passing through at least a portion of a breast;
an x-ray detector translation system operatively connected to said gantry so as to be able to translate said x-ray detector from a first displacement from said breast to a second displacement at least one of immediately adjacent to or in contact with said breast while translating said x-ray source away from said breast so as to maintain a same distance between said x-ray source and said x-ray detector; and
an x-ray image processor configured to communicate with said x-ray detector so as to:

receive a computed tomography (CT) data set from said x-ray detector, said CT data set being detected by said x-ray detector at said first displacement;

compute a CT image of said breast based on said CT data set;

receive a mammography data set from said x-ray detector, said mammography data set being detected by said x-ray detector at said second displacement; and compute a mammography image of said breast based on said mammography data set.

2. The multimodal system for breast imaging according to claim 1, further comprising a gantry controller, wherein said gantry controller is configured to:

control said gantry to rotate said x-ray source and said x-ray detector around said breast during detection of said CT data set; and prevent said gantry from rotating when said x-ray detector is at said second displacement.

3. The multimodal system for breast imaging according to claim 1, further comprising a breast immobilization device, said breast immobilization device being configured to immobilize said breast during detection of at least one of said CT data set and said mammography data set.

4. The multimodal system for breast imaging according to claim 3, wherein said breast immobilization device comprises two planar structures configured to compress said breast therebetween.

5. The multimodal system for breast imaging according to claim 3, wherein said breast immobilization device comprises two non-planar structures configured to compress said breast therebetween.

6. The multimodal system for breast imaging according to claim 3, wherein said breast immobilization device comprises a radiolucent material, said radiolucent material defining a window permitting a biopsy needle to pass therethrough.

7. The multimodal system for breast imaging according to claim 1, wherein said x-ray source is a cone beam x-ray source, said x-ray detector is a flat panel x-ray detector, and said CT data set is a cone-beam CT data set.

8. A method for performing multimodal breast imaging, comprising:

obtaining a computed tomography (CT) data set from an x-ray detector at a first displacement from a breast;

computing a CT image of said breast based on said CT data set;

obtaining a mammography data set from said x-ray detector at a second displacement at least one of immediately adjacent to or in contact with said breast;

computing a mammography image of said breast based on said mammography data set;

receiving an indication from a user of a region of said breast to be biopsied based on said CT image and said mammography image; and controlling a robotic biopsy assembly to obtain tissue from said region.

9. The method for performing multimodal breast imaging according to claim 8, further comprising:

translating said x-ray detector and an x-ray source providing x-rays detected by said x-ray detector in order to maintain a same distance between said x-ray source and said x-ray detector when said x-ray detector is at said first displacement and at said second displacement.

10. The method for performing multimodal breast imaging according to claim 9, wherein translating said x-ray detector and said x-ray source comprises linearly translating a gantry physically coupled to said x-ray detector and said x-ray source, said gantry being configured to rotate said x-ray detector and said x-ray source around said breast when said x-ray detector is at said first displacement.

11. A multimodal system for breast imaging, comprising:

an x-ray source;

an x-ray detector configured to detect x-rays from said x-ray source after passing through at least a portion of a breast;

an x-ray detector translation system operatively connected to said x-ray detector so as to be able to translate said x-ray detector from a first displacement from said breast to a second displacement at least one of immediately adjacent to or in contact with said breast; and an x-ray image processor configured to communicate with said x-ray detector so as to:

receive a computed tomography (CT) data set from said x-ray detector, said CT data set being detected by said x-ray detector at said first displacement;

compute a CT image of said breast based on said CT data set;

receive a mammography data set from said x-ray detector, said mammography data set being detected by said x-ray detector at said second displacement;

compute a mammography image of said breast based on said mammography data set;

receive an indication from a user of a region of said breast to be biopsied based on at least one of said CT image and said mammography image; and control a robotic biopsy assembly to obtain tissue from said region.

12. The multimodal system for breast imaging according to claim 11, wherein said system further comprises said robotic biopsy assembly.

13. The multimodal system for breast imaging according to claim 11, wherein said x-ray detector translation system is configured to translate said x-ray detector from said first displacement to said second displacement without changing a position of said x-ray source.

14. The multimodal system for breast imaging according to claim 11, wherein said x-ray detector translation system is further configured to translate said x-ray source in order to maintain a same distance between said x-ray source and said x-ray detector when said x-ray detector is at said first displacement and at said second displacement.

15. A method for performing multimodal breast imaging, comprising:

illuminating a breast with an x-ray source;

obtaining a computed tomography (CT) data set from an x-ray detector at a first displacement from said breast, said x-ray source and said x-ray detector being attached to a gantry;

computing a CT image of said breast based on said CT data set;

obtaining a mammography data set from said x-ray detector at a second displacement at least one of immediately adjacent to or in contact with said breast;

computing a mammography image of said breast based on said mammography data set; and translating said gantry so as to maintain a same distance between said x-ray source and said x-ray detector when said x-ray detector is at said first displacement and at said second displacement.

16. The method for performing multimodal breast imaging according to claim 15, further comprising:

displaying said CT image and said mammography image of said breast.

17. The method for performing multimodal breast imaging according to claim 15, further comprising:
rotating said x-ray detector around said breast when said x-ray detector is at the first displacement; and
preventing said x-ray detector from rotating around said breast when said x-ray detector is at said second displacement.

18. The method for performing multimodal breast imaging according to claim 15, further comprising:
immobilizing said breast during detection of at least one of said CT data set and said mammography data set using a breast immobilization device, said breast immobilization device comprising a radiolucent material, said radiolucent material defining a window permitting a biopsy needle to pass therethrough.

19. The method for performing multimodal breast imaging according to claim 8, further comprising:
translating said x-ray detector from said first displacement to said second displacement without changing a position of an x-ray source providing x-rays detected by said x-ray detector.

20. The method for performing multimodal breast imaging according to claim 8, wherein controlling said robotic biopsy assembly to obtain tissue from said region comprises:
positioning said robotic biopsy assembly to obtain tissue from said region, said robotic biopsy assembly including a biopsy needle;
obtaining at least one of a second CT data set and a second mammography data set showing a position of said biopsy needle relative to said region;
computing at least one of a second CT image and a second mammography image of said breast based on said at least one of a second CT data set and a second mammography data set;
repositioning said robotic biopsy assembly based on said at least one of a second CT image and a second mammography image; and
controlling said robotic biopsy assembly to obtain tissue from said region using said biopsy needle.

21. A method for performing multimodal breast imaging, comprising:
obtaining a computed tomography (CT) data set from an x-ray detector at a first displacement from a breast;
computing a CT image of said breast based on said CT data set;
obtaining a mammography data set from said x-ray detector at a second displacement at least one of immediately adjacent to or in contact with said breast;
computing a mammography image of said breast based on said mammography data set;
receiving an indication from a user of a region of said breast to be biopsied based on said CT image and said mammography image;
performing fluoroscopic imaging of said breast using said x-ray detector; and
using said fluoroscopic imaging to control a robotic biopsy assembly to obtain tissue from said region.

* * * * *